(12) United States Patent
Kim

(10) Patent No.: US 7,335,336 B1
(45) Date of Patent: Feb. 26, 2008

(54) SENSOR ARRAY USING LATERAL FIELD EXCITED RESONATORS

(75) Inventor: Yoonkee Kim, Freehold, NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 711 days.

(21) Appl. No.: 10/868,454

(22) Filed: Jun. 8, 2004

Related U.S. Application Data

(63) Continuation-in-part of application No. 10/863,831, filed on Jun. 1, 2004.

(51) Int. Cl.
*G01N 33/00* (2006.01)
(52) U.S. Cl. .................. 422/88; 422/50; 422/82.01; 422/68.1; 422/82.02
(58) Field of Classification Search .............. 422/88, 422/50, 82.01, 68.1, 82.02
See application file for complete search history.

(56) References Cited

U.S. PATENT DOCUMENTS 5,744,902 A * 4/1998 Vig .................... 310/360

6,544,478 B1   4/2003  Oyama et al.
7,075,216 B1 * 7/2006  Vetelino .............. 310/338

OTHER PUBLICATIONS

Hu, Y., et al, Laboratory for Surface Science & Technology, Orono, ME "A Lateral Field Excited Liquid Acoustic Wave Sensor", IEEE Conference Records—Abstracts, International Ultrasonics Symposium, Honolulu, HI, p. 12&13 (2003).

* cited by examiner

*Primary Examiner*—Jill Warden
*Assistant Examiner*—Samuel P Siefke
(74) *Attorney, Agent, or Firm*—Michael Zelenka; George B. Tereschuk

(57) ABSTRACT

A sensor for sensing a property of a plurality of analytes includes a substrate having a resonant frequency that varies based on contact with a predetermined property of an analyte. The substrate has an analyte contact surface and a non-analyte contact surface located opposed to the analyte contact surface. The analyte contact surface is configured to receive a plurality of analytes. A plurality of pairs of electrodes are operatively connected with the nonanalyte contact surface, each of the electrodes being spaced apart one from another.

2 Claims, 4 Drawing Sheets

(TFE)

(LFE)

SENSOR ARRAY USING LATERAL FIELD EXCITED RESONATORS

CROSS REFERENCE TO RELATED APPLICATION

This application is a continuation-in-part of U.S. patent application Ser. No. 10/863,831, entitled "Corrosive or Conductive Liquid/Gas Sensor Using Lateral-Field-Excited Resonator".

GOVERNMENT INTEREST

The invention described herein may be manufactured, used, imported, sold, and licensed by or for the Government of the United States of America without the payment of any royalty thereon or therefor.

BACKGROUND OF THE INVENTION

1. Field of the Invention

The present invention relates generally to acoustic sensors and, more particularly, to sensors comprising quartz crystal microbalance resonators.

2. Related Art

Sensors comprising quartz crystal microbalance (QCM) resonators are generally known. QCM resonators may function as acoustic wave resonators to provide highly sensitive detection mechanism for fluid analytes. As illustrated in FIG. 1, a typical QCM resonator is shown generally at 100 and comprises a piezoelectric crystal substrate 102 located between a pair of electrodes 104 having leads 106. In this configuration, an electric field may be generated by the electrodes 104 and extend therebetween along a transverse axis, or through the thickness, of the piezoelectric crystal substrate 102. Hence in this configuration the QCM resonator may be termed a thickness field excitation (TFE) resonator. The electrodes 104 and the crystal 102 are dimensioned to achieve an optimal resonance condition.

One particular example of a TFE resonator is described in U.S. Pat. No. 6,544,478 to Oyama et al wherein the resonator is arranged in a multi-channel structure. The resonator includes a crystal substrate that has four mutually opposed electrodes disposed on opposite sides of the substrate. In operation, the TFE resonator may be used to detect and quantitatively analyze components of a sample from a variation in fundamental resonant frequency and impedance when a surface of one of the pair of electrodes is immersed into either a sample gas or solution.

While the above TFE resonators have been suitable for use with non-caustic analytes, it has been found that when these resonators are immersed into a caustic substance the electrodes tend to deteriorate. Also, use of these resonators is restricted to non-conductive analytes because of the possibility that the electric field may become shorted. Accordingly, to date, no suitable QCM resonator is available for analyzing a caustic or conductive analyte.

SUMMARY OF THE INVENTION

In accordance with an embodiment of the present invention, a sensor for sensing a property of a plurality of analytes comprises a substrate having a resonant frequency that varies based on contact with a predetermined property of an analyte. The substrate has an analyte contact surface and a non-analyte contact surface located opposed to the analyte contact surface. The analyte contact surface is configured to receive a plurality of analytes. A plurality of pairs of electrodes are operatively connected with the nonanalyte contact surface, each of the electrodes being spaced apart one from another.

BRIEF DESCRIPTION OF THE DRAWINGS

The following detailed description is made with reference to the accompanying drawings, in which.

DETAILED DESCRIPTION OF THE PREFERRED EMBODIMENT

One embodiment of the present invention concerns a quartz crystal microbalance (QCM) resonator that is suitable for use with a caustic or conductive analyte. In another embodiment of the present invention, a sensor device employing a QCM resonator suitable for use with a caustic or conductive analyte is presented.

Figure 1:
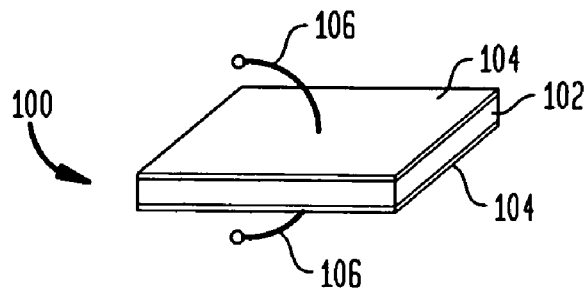
FIG. 1 is a perspective view of a QCM resonator in accordance with the prior art.
Figure 2:
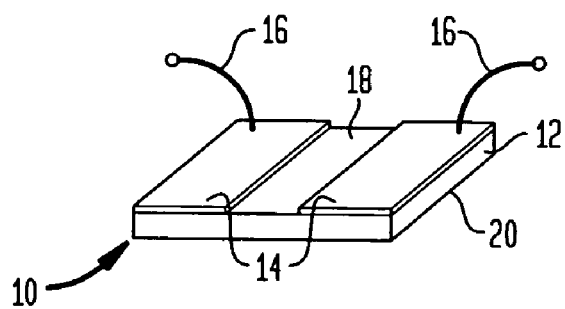
FIG. 2 is a perspective view of a QCM resonator in accordance with an embodiment of the present invention.

Referring now to FIG. 2, a QCM resonator in accordance with one embodiment of the present invention is illustrated generally at 10. In this embodiment, the QCM resonator 10 comprises a substrate 12, electrodes 14 and electrode leads 16.

The substrate 12 may comprise a piezoelectric crystal material such as quartz that functions such that when contacted with a property of an analyte to be measured, varies in resonant frequency and impedance in a known manner. Examples of properties of an analyte to be measured include viscosity and density. The substrate 12 may comprise any suitable outer geometrical configuration such as square or circular and comprises an electrode depositing surface 18 and an analyte contact surface 20. Although not illustrated as such, the analyte contact surface 20 may be coated with a material such as an antibody and/or a polymer that may enhance sensitivity or selectivity of the QCM resonator 10 in a known manner.

In accordance with a feature of this embodiment of the present invention, the electrodes 14 are located away from any contact with an analyte that may be limited to the analyte contact surface 20. As illustrated, both of the electrodes are located on the electrode depositing surface 18, although, other locations on the substrate may be possible. The electrodes 14 may comprise any suitable, highly conductive, metallic substance, although gold is preferred, and may be applied to the substrate 12 via photolithography or deposited via, e.g., evaporation, sputtering, or electroplating. Electrode leads 16 may be connected at one end to the electrodes 14 and at the other to a suitable AC source at the resonant frequency of the resonator 52 and measuring device (not shown).

In this configuration, an electric field may be generated by the electrodes 16 along a lateral axis of the piezoelectric crystal substrate 12. Hence in this configuration the QCM resonator may be termed a lateral field excitation (LFE) resonator. As in the TFE case, the electrodes 16 and the crystal 12 may be dimensioned to achieve an optimal resonance condition.

Figure 3:
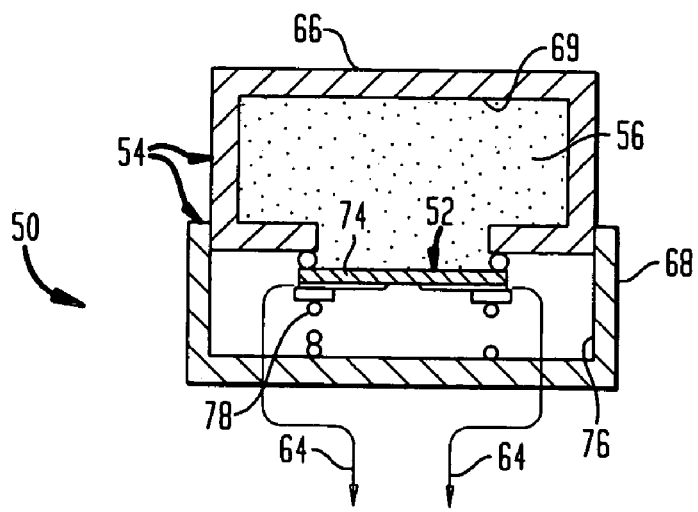
FIG. 3 is a cross section of a sensor device including a QCM resonator in accordance with another embodiment of the present invention.
Figure 4:
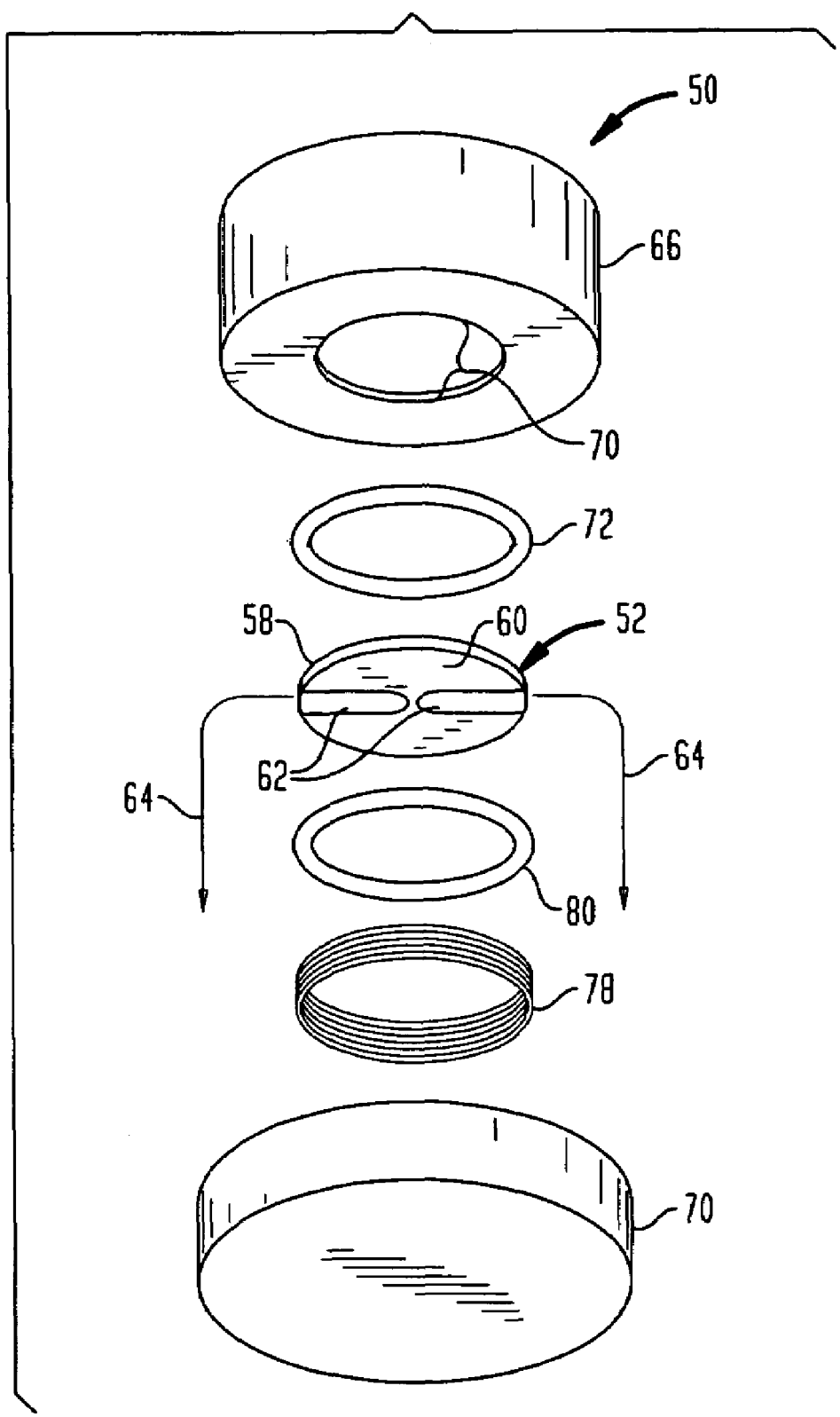
FIG. 4 is an exploded view of the sensor device of FIG. 3.

In another embodiment of the present invention, illustrated in FIGS. 3 and 4 a sensor device 50 comprises a QCM resonator 52 and a housing 54 for an analyte 56. The QCM resonator 52 may be similar to the QCM resonator 10 described above and similarly comprises a substrate 58 including an electrode depositing surface 60, electrodes 62 deposited to the electrode depositing surface and electrode leads 64.

The housing 54 may comprise an analyte support container 66 and a base 68. The analyte support container 66 and the base 68 may each comprise a moldable polymeric material such as a polyethylene or a polyamide and may also each comprise generally cylindrical outer configurations, as illustrated. The analyte support container 66 is illustrated as having a generally closed configuration including a chamber 69 for the analyte 56 and an aperture 70, although, it will be understood that the analyte support container may comprise a lid or cover (not shown) or be connected to a pipe or conduit (also not shown) for communication of the analyte to the chamber in a continuous flow-like process.

The base 68 comprises an open end (not numbered) that is preferably dimensioned to receive the analyte support container 66 (best seen in FIG. 3). A seal, such as an O-ring 72, is provided to seal the analyte 56 adjacent an analyte support surface 74 from a cavity 76 of the base 68. A spring 78 may be interposed between the base 68 and the QCM resonator 52 for biasing the resonator adjacent the O-ring 72, which is in turn biased adjacent the analyte support container 66. Another O-ring 80 may be employed to insulate the spring 78 and prevent shorting the electrodes 62. This embodiment allows an easy replacement of the QCM resonator 52 when the need for replacement of the QCM resonator 52 arises. This may be when the resonator 52 is damaged or a different coating for sensing a different analyte may be necessary.

Figure 5:
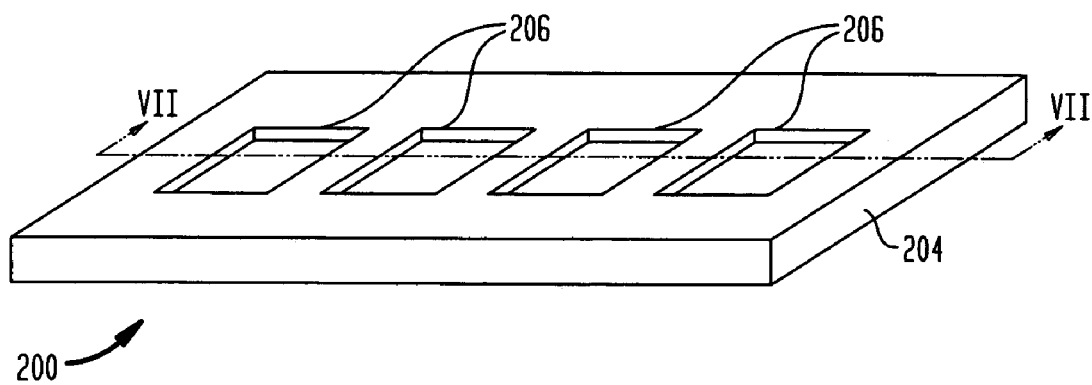
FIG. 5 is a perspective view showing an analyte contact surface of a sensor device in accordance with another embodiment of the present invention.
Figure 6:
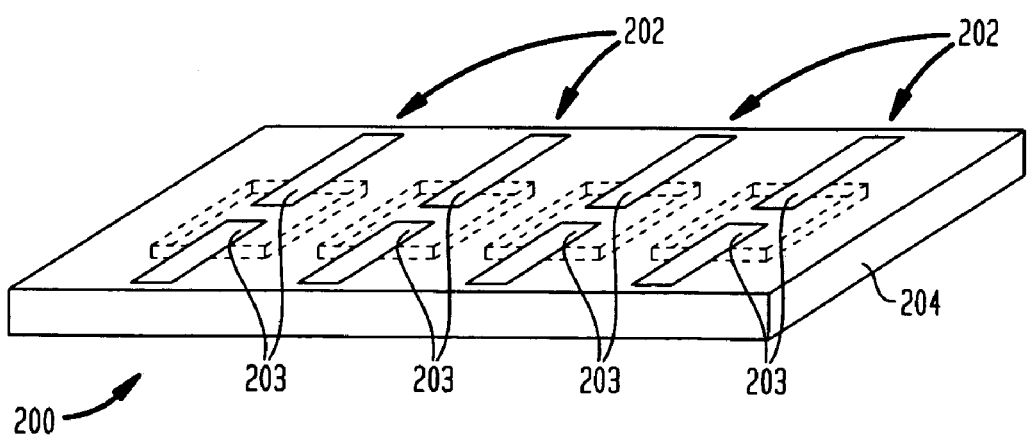
FIG. 6 is another perspective view of the sensor device of FIG. 5 showing an electrode contact surface.
Figure 7:
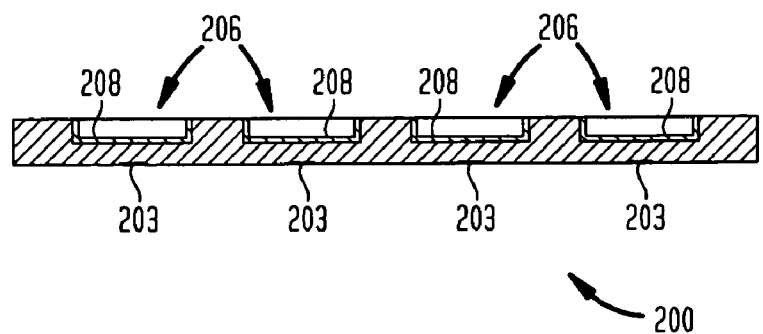
FIG. 7 is a sectional view taken along line VII of FIG. 5.

In another embodiment of a sensing device in accordance with the present invention, illustrated generally at 200 in FIGS. 5 through 7, multiple QCM resonators 202, each comprising a plurality of electrode pairs 203, are located on a substrate 204. The substrate 204 may be composed of a similar material as that of the substrate 12, described above in connection with FIG. 2, although, it will be understood that a layered structure comprising a glass slide (not shown) and a piezoelectric film (also not shown) may be substituted for the substrate. The substrate 204 may comprise wells 206 that may be formed by etching and may each comprise a generally rectangular configuration, as illustrated, although other configurations, such as circular or plate-shaped, may be used. The wells 206 may function to receive a sample, or differing samples of, fluid analyte (not shown). A coating 208 may be applied to the substrate 204 within the wells 206 as shown and may comprise an antibody and/or a polymer as described above for enhancing sensitivity or selectivity. It will be appreciated that each well 206 may comprise a coating that comprises a different material in order to, e.g., vary the analysis for one particular sample fluid analyte. For example, different coatings comprising differing antibodies dispersed in a polymer carrier may be applied to various wells 206 for testing one particular analyte for different reactions in a known manner.

Figure 8:
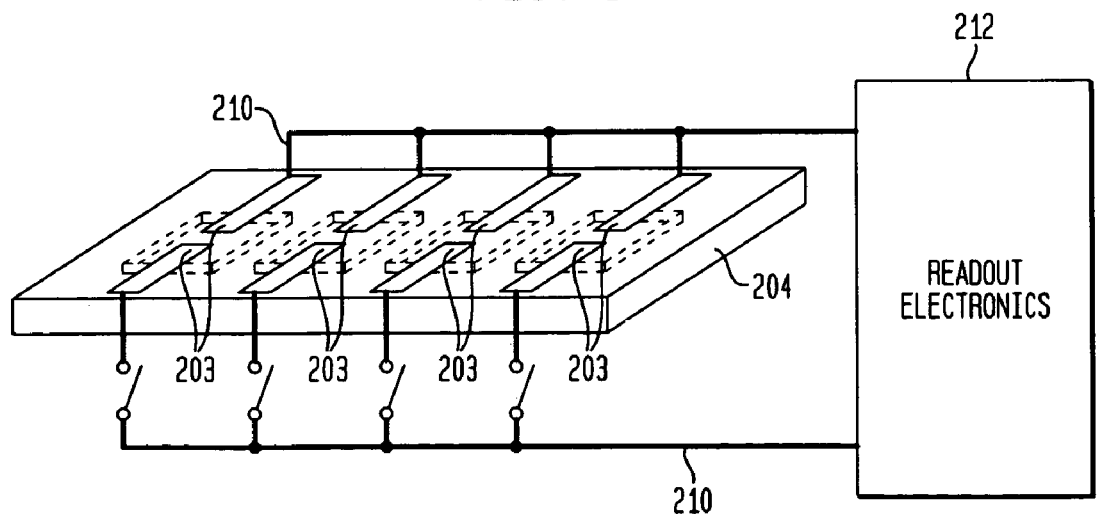
FIG. 8 is a diagram showing the sensor device of FIG. 5 in circuit with switches and readout electronics in accordance with a further embodiment of the present invention.

Referring now to FIG. 8, each electrode pair 203 may be connected in a parallel circuit via lines 210 to readout electronics 212. Switches 214 may be interposed between the electrode pairs 203 and the readout electronics 212 for operation of each QCM resonator 202. In operation, the readout electronics 212 may be operated in a known manner and switches 214 may be sequentially closed to energize a particular electrode pair 203.

While the present invention has been described in connection with what are presently considered to be the most practical and preferred embodiments, it is to be understood that the present invention is not limited to these herein disclosed embodiments. Rather, the present invention is intended to cover all of the various modifications and equivalent arrangements included within the spirit and scope of the appended claims.

What is claimed is:

1. A sensor for sensing a property of a plurality of analytes, comprising:
   a substrate having a resonant frequency that varies based on contact with a predetermined property of an analyte;
   the substrate having an analyte contact surface and a non-analyte contact surface located opposed to the analyte contact surface, the analyte contact surface configured to receive a plurality of analytes;
   a plurality of pairs of electrodes operatively connected with the non-analyte contact surface, each of the electrodes being spaced apart one from another; and
   the analyte contact surface further comprising a plurality of wells and each well corresponds to a pair of electrodes.

2. A sensor for sensing a property of a plurality of analytes, comprising:
   a substrate having a resonant frequency that varies based on contact with a predetermined property of an analyte;
   the substrate having an analyte contact surface and a non-analyte contact surface located opposed to the analyte contact surface, the analyte contact surface configured to receive a plurality of analytes;
   a plurality of pairs of electrodes operatively connected with the non-analyte contact surface, each of the electrodes being spaced apart one from another;
   the analyte contact surface further comprising a plurality of wells; and
   each well corresponding to a pair of electrodes and having a coating composed of a polymer and/or an antibody.

* * * * *